US005616739A

United States Patent [19]

Mas et al.

[11] Patent Number: 5,616,739

[45] Date of Patent: Apr. 1, 1997

[54] METHOD OF PREPARING TAXANE DERIVATIVES

[75] Inventors: Jean-Manuel Mas, Villeurbanne; Viviane Massonneau, Ecully, both of France

[73] Assignee: Rhone-Poulenc Rorer, S.A., Antony, France

[21] Appl. No.: 411,692

[22] PCT Filed: Oct. 4, 1993

[86] PCT No.: PCT/FR93/00967

§ 371 Date: May 3, 1995

§ 102(e) Date: May 3, 1995

[87] PCT Pub. No.: WO94/07877

PCT Pub. Date: Apr. 14, 1994

[30] Foreign Application Priority Data

Oct. 5, 1992 [FR] France .................................. 92 11741

[51] Int. Cl.$^6$ .................................................. C07D 305/14

[52] U.S. Cl. ........................................... 549/510; 549/511

[58] Field of Search ..................................... 549/510, 511

[56] References Cited

U.S. PATENT DOCUMENTS

| | | | |
|---|---|---|---|
| 5,015,744 | 5/1991 | Holton | 549/510 |
| 5,136,060 | 8/1992 | Holton | 549/510 |
| 5,175,315 | 12/1992 | Holton | 549/510 |
| 5,319,112 | 6/1994 | Kingston et al. | 549/510 |

FOREIGN PATENT DOCUMENTS

| | | |
|---|---|---|
| 0400971 | 12/1990 | European Pat. Off. . |
| 0428376 | 5/1991 | European Pat. Off. . |
| WO92/09589 | 11/1991 | WIPO . |

OTHER PUBLICATIONS

J. Med. Chem. vol. 34, No. 3, Mar. 1991, Washington, DC pp. 992–998, F. Gueritte-Voegelein et al.

Stud. Org. Chem. (New Trends in Nat. Prod. Chem. 1986), vol. 26, 1986, Amsterdam, pp. 219–235.

*Primary Examiner*—Ba K. Trinh

*Attorney, Agent, or Firm*—Finnegan, Henderson, Farabow, Garrett & Dunner, L.L.P.

[57] ABSTRACT

This invention relates to a method of preparing taxane derivatives of general formula (I) by esterification of protected baccatine III or 10-deacetylbaccatine III by means of an acid of general formula (VII), elimination of protection groupings of the ester obtained, and acylation of the amine function of the side chain. In formulae (I) and (VII): Ar stands for aryl, R is hydrogen or acetyl, $R_1$ is benzoyl or $R_2$—CO—O— in which $R_2$ is alkyl, alkenyl, alkynyl, cycloalkyl, cycloalkenyl, bicycloalkyl, phenyl or heterocyclyl, $R_3$ and $R_4$ may be the same or different and represent hydrogen, alkyl, alkenyl, aralkyl, aryl or alkoxy, and $R_5$ is an alkyl radical substituted by one or more chlorine atoms (2,2,2-trichloroethyl, (2-trichloromethylisopropyl).

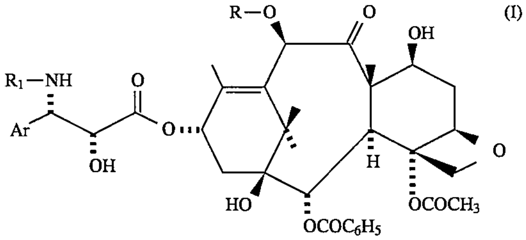

(I)

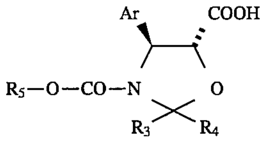

(VII)

21 Claims, No Drawings

METHOD OF PREPARING TAXANE DERIVATIVES

DESCRIPTION OF THE INVENTION

The present invention relates to a new process for preparing taxane derivatives of general formula:

(I)

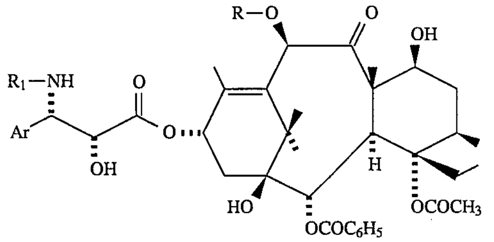

which possess noteworthy antileukaemic and antitumour properties.

In the general formula (I):

R represents a hydrogen atom or an acetyl radical, $R_1$ represents a benzoyl radical or a radical $R_2$—O—CO— in which $R_2$ represents an alkyl, alkenyl, alkynyl, cycloalkyl, cycloalkenyl, bicycloalkyl, phenyl or a nitrogenous heterocycle radical, and Ar represents an aryl radical.

More especially, R represents a hydrogen atom or an acetyl radical and $R_1$ represents a benzoyl radical or a radical $R_2$—O—CO— in which $R_2$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents chosen from halogen atoms and hydroxyl radicals, alkyloxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl, cyano or carboxyl radicals or alkyloxycarbonyl radicals in which the alkyl portion contains 1 to 4 carbon atoms, or a phenyl radical optionally substituted with one or more atoms or radicals chosen from alkyl radicals containing 1 to 4 carbon atoms or alkyloxy radicals containing 1 to 4 carbon atoms, or a saturated or unsaturated 5- or 6-membered nitrogenous heterocyclic radical optionally substituted with one or more alkyl radicals containing 1 to 4 carbon atoms, on the understanding that the cycloalkyl, cycloalkenyl or bicycloalkyl radicals can be optionally substituted with one or more alkyl radicals containing 1 to 4 carbon atoms, and Ar represents a phenyl or α- or β-naphthyl radical optionally substituted with one or more atoms or radicals chosen from halogen (fluorine, chlorine, bromine, iodine) atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, on the understanding that the alkyl radicals and alkyl portions of the other radicals contain 1 to 4 carbon atoms, and that the alkenyl and alkynyl radicals contain 3 to 8 carbon atoms and the aryl radicals are phenyl or α- or β-naphthyl radicals.

Of very special importance are the products of general formula (I) in which R represents a hydrogen atom or an acetyl radical, $R_1$ represents a benzoyl or t-butoxycarbonylamino radical and Ar represents a phenyl radical.

The products of general formula (I) in which $R_1$ represents a benzoyl radical correspond to taxol and to 10-deacetyltaxol, and the products of general formula (I) in which $R_1$ represents a t-butoxycarbonyl radical correspond to those which form the subject of European Patent 0,253,738.

According to the process which is described in International Application PCT WO 92/09,589, the derivatives of general formula (I) may be obtained by:

condensation of an oxazolidine derivative of general formula:

(II)

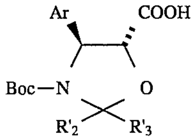

in which Ar is defined as above, Boc represents a t-butoxycarbonyl radical and $R'_2$ and $R'_3$, which may be identical or different, represent an alkyl radical containing 1 to 4 carbon atoms optionally substituted with one or more aryl radicals, or an aryl radical, or alternatively $R'_2$ and $R'_3$, together with the carbon atom to which they are linked, form a 4- to 7-membered ring, with protected 10-deacetylbaccatin III or baccatin III of general formula:

(III)

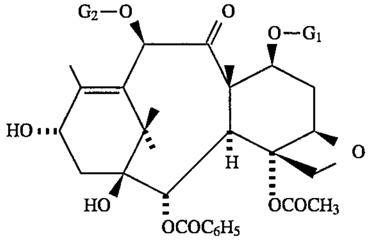

in which $G_1$ represents a group protecting the hydroxyl function and $G_2$ represents an acetyl radical or a group protecting the hydroxyl function, to obtain a product of general formula:

(IV)

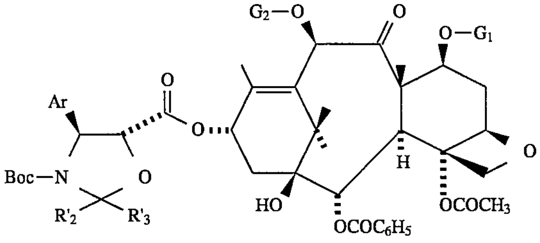

in which Ar, $R'_2$, $R'_3$, $G_1$, $G_2$ and Boc are defined as above, treatment of the product of general formula (IV) in an acid medium under conditions which have no effect on $G_1$ and $G_2$, to obtain the product of general formula:

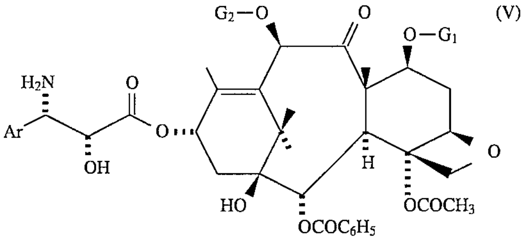

(V)

in which Ar, $G_1$ and $G_2$ are defined as above, treatment of the product of general formula (V) with a suitable reagent for introducing a benzoyl radical or radical $R_2$—O—CO—, to obtain a product of general formula:

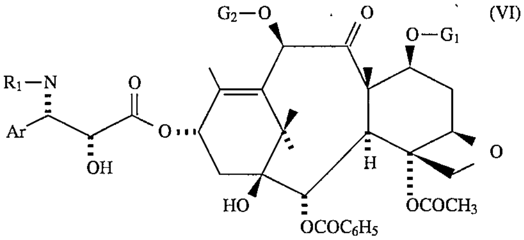

(VI)

in which Ar, $R_1$, $G_1$ and $G_2$ are defined as above, and replacement of the protective groups $G_1$ and $G_2$ of the product of general formula (VI) by hydrogen atoms to obtain the product of general formula (I).

It has now been found, and this forms the subject of the present invention, that the products of general formula (I) may be obtained:

1) by esterifying baccatin III or 10-deacetylbaccatin III of general formula (III), in which $G_1$ and, where appropriate, $G_2$ represent a group protecting the hydroxyl function, preferably a trialkylsilyl, dialkylarylsilyl, alkyldiarylsilyl or triarylsilyl radical and still more especially a radical $R_5$—O—CO— in which $R_5$ is defined below, by means of an acid of general formula:

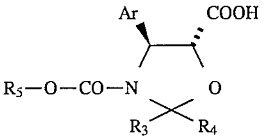

(VII)

in which Ar is defined as above, $R_3$ and $R_4$, which may be identical or different, represent a hydrogen atom or an alkyl radical containing 1 to 4 carbon atoms or an alkenyl radical containing 2 to 4 carbon atoms, or an aralkyl radical in which the alkyl portion contains 1 to 4 carbon atoms and the aryl portion preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, or alternatively $R_3$ and $R_4$, together with the carbon atom to which they are linked, form a 4- to 7-membered ring, and $R_5$ represents an alkyl radical containing 1 to 4 carbon atoms substituted with one or more chlorine atoms, to obtain a product of general formula:

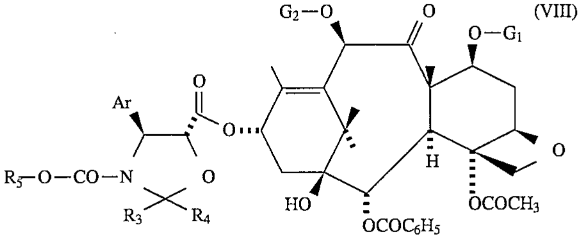

(VIII)

in which Ar, $R_3$, $R_4$, $R_5$, $G_1$ and $G_2$ are defined as above, 2) by replacing the groups protecting the hydroxyl and amino functions of the product obtained, of general formula (VIII), by hydrogen atoms to obtain the product of general formula:

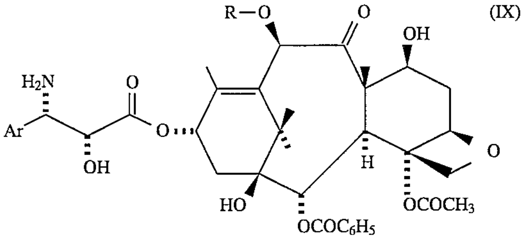

(IX)

which Ar and R are defined as above, 3) by treating the product obtained, of general formula (IX), with a reagent which enables a substituent $R_1$ to be introduced on the amino function to obtain a product of general formula (I).

According to the present invention, the esterification of protected 10-deacetylbaccatin III or baccatin III of general formula (III) by means of an acid of general formula (VII), in which $R_5$ represents a 2,2,2-trichloroethyl or 2-(trichloromethyl)isopropyl radical, may performed in the presence of a condensing agent, for instance a diimide such as dicyclohexylcarbodiimide or a reactive carbonate such as di-2-pyridyl carbonate, and an activating agent, for instance an aminopyridine such as 4-(dimethylamino) pyridine or 4-pyrrolidinopyridine, working in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane or aromatic hydrocarbons such as benzene, toluene, xylenes, ethylbenzene, isopropylbenzene or chlorobenzene, at a temperature of between −10° and 90° C. It is especially advantageous to perform the esterification working in an aromatic hydrocarbon at a temperature in the region of 20° C.

The esterification may also be carried out using the acid of general formula (VII) in the form of an anhydride of general formula:

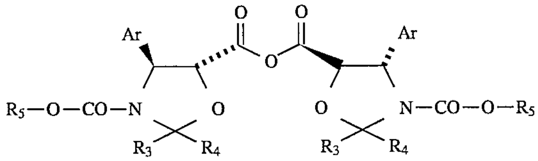

(X)

in which Ar, $R_3$, $R_4$ and $R_5$ are defined as above, $R_5$ preferably representing a 2,2,2-trichloroethyl or 2-(trichloromethyl)isopropyl radical, in the presence of an activating agent, for instance an aminopyridine such as 4-(dimethylamino)pyridine or 4-pyrrolidinopyridine, working in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated hydrocarbons such as dichloromethane or 1,2-dichloroethane or aromatic hydrocarbons such as benzene, toluene, xylenes, ethylbenzene, isopropylbenzene or chlorobenzene, at a temperature of between 0° and 90° C.

The esterification may also be carried out using the acid of general formula (VII) in the form of a halide or in the form of a mixed anhydride of general formula:

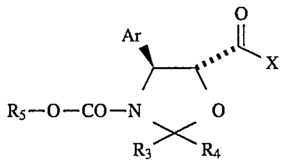

(XI)

in which Ar, $R_3$, $R_4$ and $R_5$ are defined as above $R_5$ preferably representing a 2,2,2-trichloroethyl or 2-(trichloromethyl)isopropyl radical, and X represents a halogen atom or an acyloxy or aroyloxy radical, optionally prepared in situ, in the presence of a base which is preferably a nitrogenous organic base, for instance a tertiary aliphatic amine such as triethylamine, pyridine, an aminopyridine such as 4-(dimethylamino)pyridine or 4-pyrrolidinopyridine, working in an inert organic solvent chosen from ethers such as tetrahydrofuran, diisopropyl ether, methyl t-butyl ether or dioxane, ketones, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylanes, ethylbenzene, isopropylbenzene or chlorobenzene, at a temperature of betwean 10° and 80° C., and preferably in the region of 20° C.

It is preferable to use an activated derivative of general formula (XI) in which X represents a halogen atom or an acyloxy radical containing 1 to 5 carbon atoms or an aroyloxy radical in which the aryl portion is a phenyl radical optionally substituted with 1 to 5 identical or different atoms or radicals chosen from halogen (chlorine, bromine) atoms and nitro, methyl or methoxy radicals.

The replacement by hydrogen atoms of the groups protecting the hydroxyl and amino functions of the product of general formula (VIII), in which $R_5$ preferably represents a 2,2,2-trichloroethyl or 2-(2-trichloromethylpropyl) radical and $G_1$ and, where appropriate, $G_2$ represent a group protecting the hydroxyl function, preferably a 2,2,2-trichloroethoxycarbonyl or 2-(2-trichloromethylpropoxy)carbonyl radical, and is generally performed by treatment with zinc, optionally in combination with copper, in the presence of acetic acid at a temperature of between 30° and 60° C., or by means of an inorganic or organic acid such as hydrochloric acid or acetic acid dissolved in an aliphatic alcohol containing 1 to 3 carbon atoms or in an aliphatic ester such as ethyl acetate, isopropyl acetate or n-butyl acetate, in the presence of zinc optionally in combination with copper.

The replacement by hydrogen atoms of the groups protecting hydroxyl and emino functions of the product of general formula (VIII), in which $R_5$ preferably represents a 2,2,2-trichloroethyl or 2-(2-trichloromethylpropyl) radical and $G_1$ and, where appropriate, $G_2$ represent a group protecting the hydroxyl function, preferably a trialkylsilyl, dialkylarylsilyl, alkyldiarylsilyl or triarylsilyl radical, is generally performed by treatment in an acid medium such as, for example, hydrochloric acid dissolved in an aliphatic alcohol containing 1 to 3 carbon atoms (methanol, ethanol, propanol, isopropanol) or aqueous hydrofluoric acid at a temperature of between 0° and 40° C. to replace the protective groups $G_1$ and, where appropriate, $G_2$, and by treatment with zinc, optionally in combination with copper, in the presence of acetic acid at a temperature of between 30° and 60° C., or by means of an inorganic or organic acid such as hydrochloric acid or acetic acid dissolved in an aliphatic alcohol containing 1 to 3 carbon atoms or an aliphatic ester such as ethyl acetate, isopropyl acetate or n-butyl acetate, in the presence of zinc optionally in combination with copper, to replace $R_5$.

The replacement of the protective groups of the product of general formula (VIII) hy hydrogen atoms may also be performed by electrolytic reduction.

The introduction of a substituent $R_1$ on the amino function of the product of general formula (IX) is performed by the action of benzoyl chloride or a reactive derivative of general formula:

$R_2$—O—CO—Y (XII)

in which $R_2$ is defined as above and Y represents a halogen (fluorine, chlorine) atom or a residue —O—$R_2$ or —O—CO—O$R_2$, working in an organic solvent, for instance an alcohol such as methanol, an aliphatic ester such as ethyl acetate or a halogenated aliphatic hydrocarbon such as dichloromethane, in the presence of an inorganic or organic base such as sodium bicarbonate. In general, the reaction is performed at a temperature of between 0° and 50° C., and preferably in the region of 20° C.

The acid of general formula (VII) may be obtained by saponification in a basic medium of the ester of general formula:

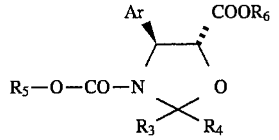

(XIII)

in which Ar, $R_3$, $R_4$ and $R_5$ are defined as above and $R_6$ represents an alkyl radical containing 1 to 4 carbon atoms optionally substituted with a phenyl radical.

In general, the saponification is performed by means of an inorganic base such as an alkali metal hydroxide (lithium, potassium, sodium hydroxide) or an alkali metal carbonate or bicarbonate (sodium bicarbonate, potassium carbonate or bicarbonate), in an aqueous-alcoholic medium such as a methanol/water mixture at a temperature of between 10° and 40° C., and preferably in the region of 20° C.

The ester of general formula (XIII) may be obtained by the action of a product of general formula:

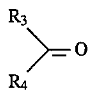

(XIV)

in which $R_3$ and $R_4$ are defined as above, optionally in the form of a dialkyl acetal or an enol alkyl ether, on a phenylisoserine derivative of general formula:

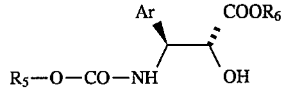

(XV)

in which Ar, $R_5$ and $R_6$ are defined as above, in racemic form or preferably in the 2R,3S form, working in an inert organic solvent in the presence of a strong inorganic acid such as sulphuric acid or strong organic acid such as p-toluenesulphonic acid, optionally in the form of a pyridinium salt, at a temperature between 0° C. and the boiling point of the reaction mixture. Solvents which are especially suitable are aromatic hydrocarbons.

The product of general formula (XV) may be prepared under the conditions described in International Application PCT WO 92/09,589.

The anhydride of general formula (X) may be obtained by reacting a dehydrating agent such as dicyclohexylcarbodiimide with the acid of general formula (VII), working in an organic solvent chosen from halogenated aliphatic hydrocarbons and aromatic hydrocarbons, at a temperature of between 0° and 30° C.

The activated acid of general formula (XI) may be obtained by the action of a sulphuryl halide, preferably the chloride, or a product of general formula:

$R_5—CO—Z$ (XVI)

in which $R_7$ represents an alkyl radical containing 1 to 4 carbon atoms or a phenyl radical optionally substituted with 1 to 5 identical or different atoms or radicals chosen from halogen atoms and nitro, methyl or methoxy radicals and Z represents a halogen atom, preferably a chlorine atom, on an acid of general formula (VII), working in a suitable organic solvent such as tetrahydrofuran in the presence of an organic base, for instance a tertiary amine such as triethylamine, at a temperature of between 0° and 30° C.

EXAMPLES

The examples which follow illustrate the present invention.

EXAMPLE 1

9.48 $cm^3$ of 2,2,2-trichloroethoxycarbonyl chloride are added in the course of 50 minutes at 0° C. to a solution of 11.7 g (60 mmol) of methyl (2R,3S)-phenylisoserinate and 5.22 g of pyridine in 180 $cm^3$ of methylene chloride. The temperature of the reaction mixture is allowed to return to rise to a value in the region of 20° C. while the mixture is stirred for 3 hours. The solution is washed with 100 $cm^3$ of 0.1N aqueous hydrochloric acid solution and then with twice 50 $cm^3$ of water. After drying of the organic phase and concentration thereof under reduced pressure, the residue is taken up with 300 $cm^3$ of cyclohexane. The solvent is then partially concentrated under reduced pressure (60 kPa) at 40° C. until the first crystals appear. The precipitate thereby obtained is isolated by filtration, then washed with cyclohexane and dried. 19.1 g of methyl (2R,3S)-2-hydroxy-3-phenyl-3-(2,2,2-trichloroethoxycarbonylamino)propionate, the characteristics of which are as follows, are thereby obtained in an 86% yield:

proton NMR spectrum (360 MHz; DMSO-$d_6$; chemical shifts in ppm; coupling constants J in Hz): 8.12 (d, J=9.2, 1H); 7.20 (M, 5H); 5.63 (M, 1H); 4.89 (dd, J=5.1 and 9.2, 1H); 4.77 and 4.67 (AB syst, J=–12.3, 1H); 4.29 (m, 1H); 3.46 (s, 3H).

151 mg of pyridinium para-toluenesulphonate are added to a solution of 11.1 g (30 mmol) of methyl (2R,3S)-2-hydroxy-3-phenyl-3-(2,2,2-trichloroethoxycarbonylamino-)propionate and 3.24 g of 2-methoxypropene in 100 $cm^3$ of toluene. The reaction mixture is heated to boiling. 50 $cm^3$ of a toluene solution containing 19.5 g of 2-methoxypropene are added in the course of 2 hours. Distillation is performed until 80 $cm^3$ of distillate are obtained. The reaction mixture is cooled to a temperature in the region of 20° C., treated with sodium bicarbonate and then washed with water. The organic solution is dried and then concentrated under reduced pressure. 14.5 g of oily crude product are thereby obtained, which product is chromatographed on a silica column, eluting with a cyclohexane/ethyl acetate mixture (90:10 by volume). 5.68 g of pure (4S,5R)-5-methoxycarbonyl-2,2-dimethyl-4-phenyl-3-(2,2,2-trichloroethoxycarbonyl)-1,3-oxazolidine (yield = 46%) and 4.95 g of pure (4S,5R)-5-methoxycarbonyl-2-methyl-2-isobutenyl-4-phenyl-3-(2,2,2-trichloroethoxycarbonyl)-11,3-oxazolidine (yield = 36.7%) are isolated.

EXAMPLE 2

A 6% (w/v) methanolic solution of potassium hydroxide is added to a solution of 1.24 g (3 mmol) of (4S,5R)-5-methoxycarbonyl-2,2-dimethyl-4-phenyl-3-(2,2,2-trichloroethoxycarbonyl)-1,3-oxazolidine. The reaction mixture is kept stirring for 4 hours at a temperature in the region of 20° C. After the addition of 5 $cm^3$ of water and stirring for 30 minutes at a temperature in the region of 20° C., the reaction mixture is concentrated to dryness. The oily residue is taken up with 20 $cm^3$ of water and extracted with twice 20 $cm^3$ of diisopropyl ether. The aqueous phase is acidified by adding 1N aqueous hydrochloric acid solution until the pH equals 2, and is then extracted with 20 $cm^3$ of methylene chloride. The organic phase is dried and then concentrated under reduced pressure. 1.15 g of (4S,5R)-5-carboxyl-2,2-dimethyl-4-phenyl-3-(2,2,2-trichloroethoxycarbonyl)-1,3-oxazolidine are thereby obtained in a 96% yield.

Similar results are obtained using (4S,5R)-5-methoxycarbonyl-2-methyl-2-isobutenyl-4-phenyl-3-(2,2,2-trichloroethoxycarbonyl)-11,3-oxazolidine.

EXAMPLE 3

0.495 g of dicyclohexylcarbodiimide is added at a temperature in the region of 20° C. to a stirred solution of 0.95 g of (4S,5R)-5-carboxy-2,2-dimethyl-4-phenyl-3-(2,2,2-trichloroethoxycarbonyl)-1,3-oxazolidine and 1.43 g of 4-acetoxy-2α-benzoyloxy-5β,20-epoxy-1β-13α-dihydroxy-9-oxo-7β,10β-bis(2,2,2-trichloroethoxycarbonyloxy)-11-taxene and 0.039 g of 4-(dimethylamino)pyridine in 20 $cm^3$ of anhydrous toluene. The reaction mixture is kept stirring for 2 hours. The dicyclohexylurea is separated by filtration and then washed with toluene. The toluene phases are combined, washed successively with 0.1N aqueous hydroxhloric acid solution and saturated aqueous sodium bicarbonate solution, dried over sodium sulphate, filtered and then concentrated to dryness under reduced pressure. 2.15 g of 4-acetoxy-2α-benzoyloxy-5β,20-epoxy-1-hydroxy-9-oxo-7β,10β-bis(2,2,2-trichloroethoxycarbonyloxy)-11-taxen-13α-yl (4S,5R)-3-(2,2,2-trichloroethoxycarbonyl)-2,2-dimethyl-4-phenyl-5-oxazolidinecarboxylate are thereby obtained in a yield in the region of 78%.

EXAMPLE 4

0.65 g of zinc powder is added to a stirred solution of 1.28 g of the product obtained in Example 3 in 5 $cm^3$ of ethyl acetate, and 1.8 $cm^3$ of glacial acetic acid are then added dropwise in the course of 5 minutes. A slight exothermic reaction and an evolution of gas are noted. The reaction mixture is then maintained at 45° C. for 90 minutes and thereafter cooled to a temperature in the region of 20° C. The zinc is separated by filtration and then washed with ethyl acetate. The combined organic phases are concentrated to dryness under reduced pressure. The residue is taken up with toluene. The solution obtained is again concentrated to dryness under reduced pressure. This operation is repeated a first time with heptane and then with ethyl acetate. The residue is taken up with ethyl acetate. This solution is then extracted with 10 $cm^3$ of 0.1N aqueous hydrochloric acid solution. The aqueous phase is neutralized by adding 1N sodium hydroxide solution. 10 $cm^3$ of ethyl acetate are added and the pH is then adjusted to 8 by adding saturated aqueous sodium bicarbonate solution. After separation, the aqueous phase is extracted twice with 25 $cm^3$ of ethyl acetate. The organic phases are combined, dried over sodium sulphate, filtered and then concentrated to dryness under reduced pressure. 0.355 g of 4-acetoxy-2α-benzoyloxy-5β-20-epoxy-1β,7α,10α-trihydroxy-9-oxo-11-taxen-13α-yl (2R,3S)-3-amino-2-hydroxy-3-phenylpropionate is thereby obtained in a 49% yield.

EXAMPLE 5

0.108 g of di-tert-butyl dicarbonate is added to a solution of 0.3 g of the product obtained in Example 4 in 5 $cm^3$ of methanol. The reaction mixture is kept stirring for 15 hours at a temperature in the region of 20° C. After the addition of 20 $cm^3$ of water, the reaction mixture is extracted with 3 times 15 $cm^3$ of methylene chloride. The aqueous phases are combined, dried over sodium sulphate and then concentrated to dryness under reduced pressure. 0.395 g of 4-acetoxy-2α-benzoyloxy-5β-20-epoxy-1,7β,10β-trihydroxy-9-oxo-11-taxen-13α-yl (2R,3S)-3-tert-butoxycarbonylamino-2-hydroxy-3-phenylpropionate is thereby obtained in a 70% yield.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for preparing taxane derivatives of formula:

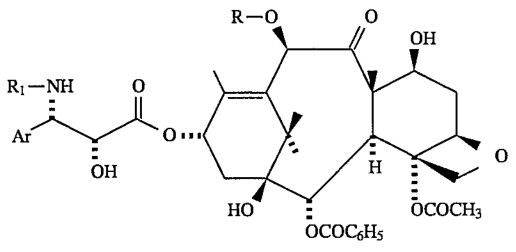

in which:

R represents a hydrogen atom or an acetyl radical, and $R_1$ represents a benzoyl radical or a radical $R_2$—O—CO— in which $R_2$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with at least one substituent selected from halogen atoms and hydroxyl radicals, alkyloxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl, cyano or carboxyl radicals or alkyloxycarbonyl radicals in which the alkyl portion contains 1 to 4 carbon atoms, or a phenyl radical optionally substituted with at least one atom or radical selected from alkyl radicals containing 1 to 4 carbon atoms or alkyloxy radicals containing 1 to 4 carbon atoms, or a saturated or unsaturated 5- or 6-membered nitrogenous heterocyclic radical optionally substituted with at least one alkyl radical containing 1 to 4 carbon atoms, the cycloalkyl, cycloalkenyl or bicycloalkyl radicals can be optionally substituted with at least one alkyl radical containing 1 to 4 carbon atoms, and Ar represents a phenyl or α- or β-naphthyl radical optionally substituted with at least one atom or radical selected from halogen including fluorine, chlorine, bromine, iodine atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, the alkyl radicals and alkyl portions of the other radicals contain 1 to 4 carbon atoms, and that the alkenyl and alkynyl radicals contain 3 to 8 carbon atoms and the aryl radicals are phenyl or α- or β-naphthyl radicals, comprising esterifying a protected 10-deacetylbaccatin III or baccatin III derivative of formula:

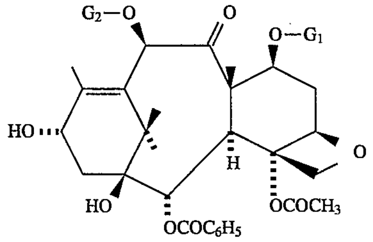

in which $G_1$ and, where appropriate, $G_2$ represent a group protecting the hydroxyl function, by means of an acid of formula:

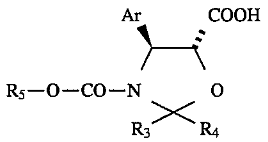

in which Ar is defined as above, $R_3$ and $R_4$, which may be identical or different, represent a hydrogen atom or an alkyl radical containing 1 to 4 carbon atoms or an alkenyl radical containing 2 to 4 carbon atoms, or an aralkyl radical in which the alkyl portion contains 1 to 4 carbon atoms and the aryl portion represents a phenyl radical optionally substituted with at least one alkoxy radical containing 1 to 4 carbon atoms, or an aryl radical representing a phenyl radical optionally substituted with at least one alkoxy radical containing 1 to 4 carbon atoms, or alternatively $R_3$ and $R_4$, together with the carbon atom to which they are linked, form a 4- to 7-membered ring, and $R_5$ represents an alkyl radical containing 1 to 4 carbon atoms substituted with at least one chlorine atom, or an activated derivative of this acid, to obtain a product of formula:

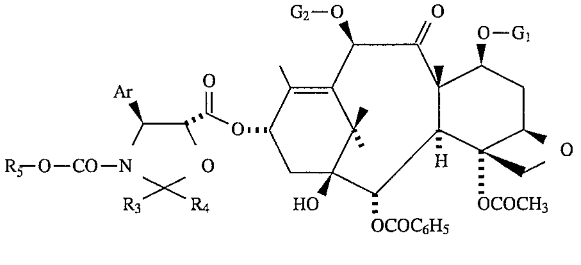

in which Ar, $R_3$, $R_4$, $R_5$, $G_1$and $G_2$ are defined as above, b) replacing the groups protecting the hydroxyl and amino functions of the product obtained by hydrogen atoms to obtain a product of formula:

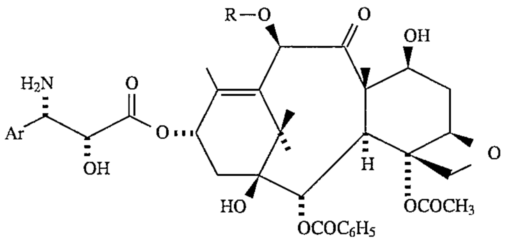

in which Ar and R are defined as above, then c) treating the product thereby obtained with a reagent which enables a substituent $R_l$ to be introduced on the amino function, and d) isolating the product obtained.

2. Process according to claim 1, wherein the esterification is performed by means of an acid of formula:

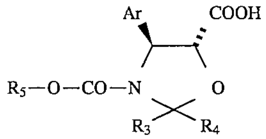

in which Ar, $R_3$, $R_4$ and $R_5$ are defined as in claim 1, working in the presence of a condensing agent and an activating agent in an organic solvent at a temperature of between −10° and 90° C.

3. Process according to claim 2, wherein the condensing agent is selected from imides and reactive carbonates and the activating agent is selected from aminopyridines.

4. Process according to claim 3, wherein the condensing agent is selected from dicyclohexylcarbodiimide and di-2-pyridyl carbonate and the activating agent is selected from 4-(dimethylamino)pyridine and 4-pyrrolidinopyridine.

5. Process according claim 2, wherein the solvent is selected from ethers, ketones, esters, nitriles, aliphatic hydrocarbons, halogenated aliphatic hydrocarbons and aromatic hydrocarbons.

6. Process according to claim 5, wherein the solvent is selected from aromatic hydrocarbons.

7. Process according to claim 1, wherein the esterification is performed by means of an anhydride of formula:

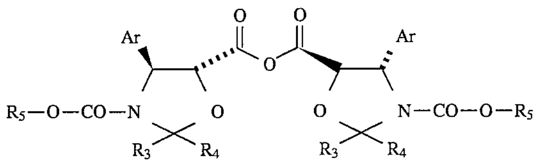

in which Ar, $R_3$, $R_4$ and $R_5$ are defined as in claim 1, working in the presence of an activating agent in an organic solvent at a temperature of between 0° and 90° C.

8. Process according to claim 7, wherein the activating agent is selected from aminopyridines.

9. Process according to claim 8, wherein the activating agent is chosen from 4-(dimethylamino)pyridine and 4-pyrrolidinopyridine.

10. Process according to claim 7, wherein the solvent is selected from ethers, ketones, esters, nitriles, aliphatic hydrocarbons, halogenated aliphatic hydrocarbons and aromatic hydrocarbons.

11. Process according to claim 1, wherein the esterification is performed by means of an activated acid of formula:

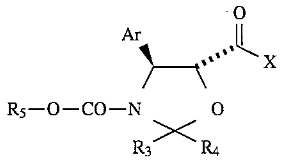

in which Ar, $R_3$, $R_4$ and $R_5$ are defined as above and X represents a halogen atom or an acyloxy or aroyloxy radical, optionally prepared in situ, in the presence of a base, working in an organic solvent at a temperature of between 10° and 80° C.

12. Process according to claim 11, wherein the base is selected from nitrogenous organic bases.

13. Process according to claim 12, wherein the nitrogenous organic base is selected from aliphatic tertiary amines, pyridine and aminopyridines.

14. Process according to claim 11, wherein the organic solvent is selected from ethers, ketones, esters, nitriles, aliphatic hydrocarbons, halogenated aliphatic hydrocarbons and aromatic hydrocarbons.

15. Process according to claim 14, wherein the solvent is selected from aromatic hydrocarbons.

16. Process according to claim 1, wherein the replacement by hydrogen atoms of the groups protecting the hydroxyl and amino functions is performed by treatment with zinc, optionally in combination with copper, in the presence of acetic acid at a temperature of between 30° and 60° C.

17. Process according to claim 1, wherein the replacement by hydrogen atoms of the groups protecting the hydroxyl and amino function is performed by means of an inorganic or organic acid dissolved in an aliphatic alcohol containing 1 to 3 carbon atoms or in an aliphatic ester, in the presence of zinc optionally in combination with copper.

18. Process according to claim 16, wherein $R_5$ represents a 2,2,2-trichloroethyl or 2-(2-trichloromethylpropyl) radical and $G_1$ and, optionally, $G_2$ represent a 2,2,2-trichoroethoxycarbonyl or 2-(2-trichloromethylpropoxy)carbonyl radical.

19. Process according claim 1, wherein the introduction of a substituent $R_1$ on the amino function is performed by the action of benzoyl chloride or a reactive derivative of general formula:

$R_2$—O—CO—Y in which Y represents a halogen atom and $R_2$ is defined as in claim 1, working in an organic solvent in the presence of an inorganic or organic base at a temperature of between 0° and 50° C.

20. Process according to claim 19, wherein the solvent is selected from alcohols, aliphatic esters and halogenated aliphatic hydrocarbons.

21. Process according to claim 19, wherein the base is sodium bicarbonate.

* * * * *

UNITED STATES PATENT AND TRADEMARK OFFICE

CERTIFICATE OF CORRECTION

PATENT NO. : 5,616,739

DATED : April 01, 1997

INVENTOR(S) : Jean-Manuel MAS et al.

It is certified that error appears in the above-indentified patent and that said Letters Patent is hereby corrected as shown below:

On the Title page, Item [57], in the Abstract, line 8, "$R_2$-CO-O-" should read --$R_2$-O-CO- --.

Claim 1, column 10, line 41, before "esterifyinq", insert --a)--.

Claim 1, column 11, line 41 "$R_l$" should read --$R_1$--.

Claim 5, column 11, line 64, after "according", insert --to--.

Claim 9, column 12, line 18, "chosen" should read --selected--.

Claim 18, column 12, line 62, "2,2,2-trichorethoxy" should read --2,2,2-trichloroethoxy--.

Claim 19, column 12, line 64, after "according" insert --to--

UNITED STATES PATENT AND TRADEMARK OFFICE
CERTIFICATE OF CORRECTION

PATENT NO. : 5,616,739
DATED : April 01, 1997
INVENTOR(S) : Jean-Manuel MAS et al.

It is certified that error appears in the above-indentified patent and that said Letters Patent is hereby corrected as shown below:

Claim 19, column 12, line 66, after "derivative of", delete "general".

Signed and Sealed this

Fourth Day of November, 1997

Attest:

BRUCE LEHMAN

*Attesting Officer*

*Commissioner of Patents and Trademarks*